United States Patent [19]

Johnson

[11] 4,378,655
[45] Apr. 5, 1983

[54] SEMI-DWARF HYBRID SUNFLOWER SEED AND PLANT AND METHOD OF PRODUCING HYBRID SEED

[75] Inventor: Freeman K. Johnson, Moorhead, Minn.

[73] Assignee: Red River Commodities, Inc., Fargo, N. Dak.

[21] Appl. No.: 295,363

[22] Filed: Aug. 24, 1981

[51] Int. Cl.³ ............................................. A01H 1/02
[52] U.S. Cl. .................................. 47/58; 47/DIG. 1
[58] Field of Search ........................... 47/58, DIG. 1

[56] References Cited

U.S. PATENT DOCUMENTS 4,143,486  3/1979  Maan .................................... 47/58
4,254,580  3/1981  Ferguson ............................. 47/58

OTHER PUBLICATIONS

"Sunflower Science and Technology"; Jack F. Carter, editor; Agronomy No. 19, (1978).

James R. Welsh, "Fundamentals of Plant Genetics and Breeding", 1981.
J. M. Poehlman, "Breeding Field Crops", 1959.
Benjamin H. Beard, "The Sunflower Crop".
Crop Science, vol. 20, Nov.-Dec. 1980.

*Primary Examiner*—Robert E. Bagwill
*Attorney, Agent, or Firm*—Brumbaugh, Graves, Donohue & Raymond

[57] ABSTRACT

This invention relates to a novel semi-dwarf hybrid sunflower (*Helianthus annuus* var. *macrocarpus* (DC.) Ckll. (herein *H. annuus*) seed and a method of producing the hybrid seed. The hybrid sunflower seed upon growth yields a semi-dwarf sunflower plant having a reduced internode length. The hybrid seed is produced by cross pollinating a pair of parent plants $P_1$ and $P_2$ wherein, in at least one parent substantially all pollen is nonfunctional and at least one parent has gametes with nuclei carrying at least one dominant gene for reduced internode length.

24 Claims, 2 Drawing Figures

SEMI-DWARF HYBRID SUNFLOWER SEED AND PLANT AND METHOD OF PRODUCING HYBRID SEED

BACKGROUND OF THE INVENTION

Sunflower (*Helianthus annuus var. Macrocarpus (DC.) CkIl.*) is a recognized crop throughout the world and has achieved significant commercial importance in the United States over the last 10 years. The sunflower is one of the four most important oil seed crops in the world. The seed of the sunflower is the source of a high quality vegetable oil which is free from toxic constituents. The oil is used in numerous foods as well as in paints, varnishes and in the manufacture of plastics. A recent discussion of sunflower as a commercial crop appeared in an article entitled "The Sunflower Crop", B. H. Beard, *Scientific American*, May 1981, p. 150, which is incorporated herein by reference.

Sunflower plants are grown by farmers using techniques similar to those used to grow corn. The plants are planted in rows and harvested with a combine when the plants are mature. In the northern areas of North America, sunflowers reach maturity in about 120 days. This stage occurs when the back of the head of the sunflower turns from green to yellow and the bracts turn brown. Usually the mature sunflower plant is allowed to dry in the field prior to harvesting with a combine.

The sunflower is a vascular plant and is a member of the Compositae family. Other members of this family include asters, chrysanthemums, daisies, marigolds, and lettuce. Botanically the sunflower is known by its genus Helianthus, from the Greek words for sun (helios) and flower (anthos). There are about 67 different known species of the genus Helianthus; most species are native to North America. Domestic sunflowers are distinguished by their single stem and the large inflorescence (flower arrangement) herein usually referred to as the head.

The stem of a sunflower is usually unbranched, although branched versions producing multiple flowers are often used in the commercial production of hybrid sunflower seeds. The diameter of the stem is usually from about 1 to 10 cm and stem length usually varies from about 50 to 500 cm. The number and length of the internodes on the stem determines the stem length. The internode is that section of the plant stem located between two successive stem joints. The area where the leaves are attached to the stalk is known as the node. The internode length of the stem usually increases as the stem of the sunflower grows.

The leaves of the sunflower plant are produced in opposite pairs and eventually as growth proceeds are produced in an alternate leaf arrangement. Leaves vary in size, shape and general morphology and these characteristics vary at different stages of leaf development. The most common leaf shape is heart-shaped, also known as cordate. Leaf blades are largest in the midregion of the plant and are measured from the tip to the base of the leaf. The width of the leaf is measured at the widest part of the blade. The surface of the leaves may be concave or convex and may or may not have hairs or other hairlike projections. The color of the leaves usually varies from light green to dark green.

The sunflower head is not a single flower but rather an aggregate of from 700-8,000 small flowers. The outer flowers on the head, herein ray flowers, have greatly enlarged petals which are golden yellow, pale yellow, orange yellow, reddish or white in color. The ray flowers are sterile and serve only as an attraction for bees and other pollinating insects. The balance of the flowers on the head, herein disk flowers, are usually fertile and produce seeds.

The seeds of sunflowers are of two different types, oil and non oil seeds. Oil seeds are small, thin hulled, and black and usually have an oil content of 40% or more. The larger confectionery seeds are gray or white with black, gray or brown stripes. They have an oil content of about 30%. Either seed can of course be used to grow additional sunflower plants. The large seeds are enjoyed as a snack food and the smaller seeds are used as bird and poultry feed.

Each disk flower which produces a seed has (1) a corolla composed of five fused small petals (2) a pistil (female) consisting of a terminal stigma, a middle style and an expanded basal ovary containing an ovule or egg; (3) a stamen (male) consisting of five filaments and five fused terminal anthers which produce pollen. The pollen produced in the anther is deposited onto the stigma where it germinates and penetrates the stigma and grows down the style into the ovule contained in the ovary where fertilization and subsequent seed development occur. Since each sunflower can have from 700-8,000 flowers, a single plant can produce that many seeds. A detailed description of both sunflower morphology and breeding is contained in Carter, Jack F. (ed.), 1978 *Sunflower Science and Technology*, Agromony 19, and is incorporated herein by reference.

In order to appreciate and understand the significance of the claimed invention and the techniques described herein, it is essential to understand basic genetics and plant breeding techniques.

Genetics is usually defined as the study of heredity in living organisms. Genetics explains the way in which the characteristics of an organism are transmitted from one generation to the next. It also attempts to explain the actions of the basic units of heredity which bring about variations in the characteristics of an organism.

The basic unit in the formation of a living organism is the cell. The cell is comprised of protoplasm, a chemically and structurally complex material which comprises the living material of a cell. The nucleus is that part of the cellular protoplasm which exercises the primary role in directing the metabolism of the cell. The nucleus contains substantially all of the genetic material contained in the cell and is the focus of the science of genetics. The remainder of the cell protoplasm is termed cell cytoplasm.

Chromosomes are structures within the cell nucleus which play a major role in heredity and help to control the characteristics of an organism. At certain times in the life cycle of a cell the chromosomes may be visible within the cell nucleus with the aid of a microscope and often appear as lineal bodies or strands. Chromosomes are principally composed of protein and complex chemical molecules of deoxyribonucleic acid (DNA).

Genes are the basic functional units of the chromosomes. Genes occupy relatively fixed positions on the chromosomes and each gene has a specific influence upon the expression of a particular characteristic or characteristics of the organism. Alternate forms of genes are known as alleles. For example, a gene associated with the normal yellow seed color in peas (YY) has an allele or an alternate form of the gene which results in green seed color (yy). The specific combinations of alleles determine the way in which genetic traits are expressed in the organism.

The total number of chromosomes present in the nucleus of a cell varies from organism to organism. In addition, the number of chromosomes found in the nuclei in various parts of an organism ordinarily vary depending upon the function of the nuclei. For example, the nuclei in body cells usually have a different number of chromosomes from cells involved in the reproductive parts of the organism. Body cells or somatic cells usually contain chromosomes in similar or homologous pairs. One member of each pair of chromosomes in the somatic cells is received from each parent. Homologous chromosomes are usually similar or identical in genetic material. The number of chromosomes in somatic cells is usually referred to as the diploid number. The somatic cells of sunflowers are normally diploid. Their nuclei contain 34 chromosomes occurring as 17 homologous pairs of chromosomes. Some species of sunflower also contain tetraploid (68) and hexaploid (102) chromosome numbers.

Gametes or reproductive cells have nuclei which ordinarily contain half the total number of chromosomes, referred to as the haploid number. Normally the chromosomes in the gametes do not occur as homologous pairs but rather as a single set of chromosomes.

The disk flowers of the sunflower plant normally produce both "male" and "female" gametes. The haploid pollen is produced in the anther of the disk flower and a single haploid egg or ovule is formed in the embryo sack in the ovary of the disk flower. The flowering of the disk flower begins with the appearance from the corolla of the anther tube, formed by the fusion of five anthers. Pollen is released on the inner surface of the anther tube. The style begins to grow and lengthen rapidly and thereby forces the stigma through the tube formed by the anthers. The lobes of the stigma open outward and at that point are receptive to pollen.

Since at this stage of development in the sunflower the stigma is above the anther in each disk flower, they are initially out of reach of their own pollen, which discourages the self-pollinization of individual disk flowers. Individual disk flowers, however, may be exposed to their own pollen and the pollen of other disk flowers on the same head by the action of insects, wind and/or gravity and both self or sibling pollination may occur.

Prior to pollen being shed, the nucleus of the pollen divides to form a vegetative or tube nucleus and a generative nucleus. The generative nucleus usually divides again to form two sperm each having a haploid number of chromosomes, seventeen in number. When the pollen is deposited on the stigma the pollen germinates and a pollen tube emerges from the pollen. The pollen tube, carrying the vegetative nucleus and the two sperm, penetrates the stigma and grows down the style into the ovule which is composed of several cells which contain a haploid number of chromosomes, seventeen in number. These ovule cells include among others an egg and a central cell with a fusion nucleus. The pollen tube penetrates the embryo sack and both sperm enter the embryo sack. One haploid sperm unites with the haploid egg to form the diploid zygote (34 chromosomes) which develops into the diploid seed which has a set of haploid chromosomes and associated traits from each parent plant. The second sperm fertilizes the fusion nucleus.

In considering the genetic or inherited characteristics of an organism, attention is given to both the "genotype" and "phenotype" of the organism. The genotype is the total genetic makeup of an individual organism and is defined by the total gene complement. In contrast, the phenotype of an organism is comprised of its manifested characteristics. For example, an organism may carry the genetic material (allele or gene) for a particular characteristic in its genotype, but it may not be actually manifested in the phenotype. Although the genotype sets certain limits on the potential for an organism's development, the total environmental circumstances determine the degree to which the potentials are realized and expressed in the actual phenotype.

An aspect of the influence of genotypes on the expression of phenotype, which is important to the understanding of this invention, may be understood through the consideration of the phenomonon of gene domainance and recessiveness. It is well known that certain genes are associated with the given mode of expression of a particular trait and will dominate over genes or alleles associated with another alternate mode of expression of the same trait. The gene which dominates over an alternate mode of expression is termed the dominant gene while the gene which is dominated is termed the recessive gene. Generally speaking, this means that if a dominant gene is present as one member of a homologous chromosome pair, the trait associated with that gene will be exhibited by the organism irrespective of the fact that a gene or allele associated with the alternate mode of expression of the same trait is present as the other member of the chromosome pair.

A recessive trait will be exhibited only if both chromosomes in a homologous pair carry the recessive gene. This concept can be illustrated by the earlier example of seed color in peas. The gene associated with this trait is a classic example of gene dominance and recessiveness. The gene associated with yellow seed color (Y) is dominant over the allele (the alternate gene form) responsible for green seed color (y) in peas. For example, if a particular plant ($F_1$) developed from a zygote or seed which received from the female seed parent ($P_1$), one member of a chromosome pair carrying the dominant gene for yellow seed color (Y) and received the other member of the chromosome pair carrying the recessive gene for green seed color (y) from the male pollen bearing parent ($P_2$), the plant ($F_1$) would be designated as having a heterozygous genotype for seed color (Yy). The symbol Yy shows the plant's genotype for seed color. The capital letter indicates that the trait represented by that symbol is dominant and the lower case letter indicates that the trait represented by that symbol is recessive. In this case where the gene combination is Yy, the gene responsible for yellow seed color is dominant. The phenotype expressed by the genotype Yy would, therefore, be that associated with the dominant gene (Y) and a plant having yellow seeds would be produced. The presence of the recessive gene (y) has no effect on the phenotype.

If alternatively, the zygote had one chromosome pair member from each parent and each chromosome bore the dominant gene (Y), the genotype would be designated as homozygous and represented as YY. The phenotype would likewise be for yellow seed color. If, however, the zygote received a pair of chromosomes and each parental chromosome bore the recessive gene (y), the genotype would be designated as being homozygous and represented as yy. The phenotype expressed would be green seed color.

It is important to note that the phenotypic expression of the green seed color may only be achieved if the recessive gene is obtained from both parents and the genotype is yy. Any gene combination containing the dominant gene for yellow seed color (Y—) would allow the dominant trait (Y) to prevail over the recessive trait (y) and a yellow seeded plant would result.

The application of the science of genetics for the improvement of plant species is known as plant breeding. This science is fully described in Poehlman, J. H., Breeding Field Crops, 1959, Henry Holt and Company, Inc., N.Y., N.Y., and Welsh, J. R., Fundamentals of Plant Genetics and Breeding, 1981, John Wiley & Con, Inc. Both of these texts are incorporated herein by reference. As early as the 16th century attempts have been made through breeding and selection techniques to improve the characteristics or phenotype of sunflower plants. Although various techniques can be used to change and improve sunflowers, hybridization has become the main technique employed by plant breeders for normally cross pollinated species such as corn, sorghum and sunflower. Examples of some of the desirable characteristics sought through the hybridization of sunflower are faster maturity, increased oil content, increased seed yield, uniformity of crop, resistance to frost, resistance to lodging (bending or flattening), resistance to diseases and insects, as well as variations in the size, shape and height of the plant.

Although there are several methods which can be used for improving sunflower traits and characteristics, hybridization has become an efficient and economical method.

Prior to the commercialization of hybrid sunflower in 1970, sunflower was grown through open pollination by insects. Because of the heterogeneity involved in random crossing (mating) an undesirable level of genetic and phenotypic variation of the sunflower varieties existed. Maximum genetic uniformity in hybrids is obtained only by utilizing homogenous plant populations. This can be achieved by several known methods.

Asexual (vegetative) propagation, wherein all plants are derived from a single plant is one such method. Many crops, including potatoes and the Jerusalem artichoke (*Helianthus tuberosus*), are propagated asexually.

Seed (sexual) propagation of inbred lines is a second method which produces a uniform plant population. Inbred lines are derived by a process of self pollination usually over six or more generations in order that all allelic pairs of genes on homologous chromosome pairs are homozygous or identical. The degree of inbreeding (homozygosity) in a line is approached at the rate of 50% per generation so that by the sixth generation 98.4% purity exist and in the seventh generation 99.2% purity exist. Thereafter, all plants derived from self pollination, sibling pollination or random crossing in isolation are essentially genetically identical and, therefore, homozygous and uniform in appearance. Maximum plant yields, however, do not occur from inbreeding. During the inbreeding process reduction in performance, yield and plant size occur. This reduction in plant vigor through inbreeding is known as inbreeding depression and is the reason that the uniform inbred lines are not grown as a commercial crop.

The third and most popular method of developing a uniform plant population is the hybridization of 2 inbred lines to produce a uniform first generation ($F_1$) hybrid. Because of hybrid vigor (heterosis), maximum yields as well as uniformity are achieved. Heterosis may be defined as the vigor of the $F_1$ hybrid over the average of its two parents or as the vigor achieved by the $F_1$ plant over the population from which the parental inbred lines have been derived.

Hybridization of inbred lines has been successfully applied to commercial sunflower crops. Self-pollination of a $F_1$ hybrid to produce the second generation ($F_2$) hybrid occurs where pollen from the same plant, or other plants of the same $F_1$ hybrid fertilizes the disk flowers of the $F_1$ hybrid. This gives rise in the $F_2$ hybrid to genetic variation and the inbreeding depression, which results in lower yields and the expression of undesirable genetic traits. Because of this reduced performance, farmers do not save seed from $F_1$ hybrids to produce a second generation hybrid ($F_2$). New hybrid seed are obtained each generation by crossing the original selected inbred parents to produce the desired hybrid seed. This is a specialized and highly skilled procedure. A great deal of effort is involved in selecting not only superior inbred parental lines, but in selecting the resulting hybrid combinations as well. As a result the hybrid seed used to produce $F_1$ hybrid plants are usually purchased from a commercial hybrid seed company.

As described above sunflowers are normally cross pollinated by insects. If randon cross pollination occurs between several different plants, however, the full benefits of uniformity and hybrid vigor are not obtained. This problem can be eliminated by using an inbred line in which little or no functional pollen is produced by the female or seed parent. Therefore seed of known parentage can be produced from specific inbred combinations. Plants with substantially nonfunctional pollen can be obtained in several ways. Chemical gametocides or the use of recessive genes can be used to produce pollen abortions or nonfunctional pollen. However, in using genetic sterility techniques such as the use of recessive genes, normally a maximum of 50% sterile plants can be produced and the fertile plants must be destroyed. In addition to complete genetic sterility genes exist which give rise to plants in which the majority of the pollen aborts or is nonfunctional, this is sometimes referred to as partial pollen abortion. Plants having a high level of self-incompatibility can also be used to prevent random cross pollination.

The preferred method, however, employs the concept of cytoplasmic male sterility (Cms). This phenomenon was discovered by P. Leclercq in 1968 and the corresponding dominant fertility restoring genes (Rf) were discovered by M. L. Kinmar and others in 1970. These discoveries were a great breakthrough in commercial sunflower breeding and have made possible mass controlled pollination and the inexpensive production of true $F_1$ hybrid seed. By selecting specific parental lines with desired agronomic traits specific hybrids with these traits could be produced on a large scale.

Cytoplasmic sterility involves transferring the genetic material in the nucleus from the common domesticated sunflower *Helianthus annuus* (herein *H. annuus*) into the nucleus and the associated cytoplasm of the wild diploid sunflower, *Helianthus petiolaris* (herein *H. petiolaris*). This was accomplished by the standard plant breeding technique of backcrossing where *H. petiolaris* was used as female and *H. annuus* was used as the recurring pollen source. Sufficient backcrosses were used to eliminate the genetic contribution of the *H. petiolaris* parent, leaving only the *H. petiolaris* cytoplasm. This process can be illustrated by a cell diagram (FIG. 1) depicting the make up of the nucleus 1 and the cytoplasm 3 of each successive generation.

When the genetic contribution of the *H. petiolaris* cytoplasm is eliminated, the plant containing the *H. petiolaris* cytoplasm and a nucleus carrying the genetic material of *H. annuus* does not produce viable pollen and is sterile. Other aspects of the plant, however, are that of normal *H. annuus*. Seed of the sterile plant is maintained by pollination of the sterile plant by normal *H. annuus* plants with both *H. annuus* genes and *H. annuus* cytoplasm. This sterile cytoplasmic condition is inherited only from the female (seed) parent ($P_1$).

Although the use of *H. petiolaris* is preferred cytoplasm from other Helianthus species could be used. For example, *Helianthus maximiliani* and *Helianthus giganteus* have been reported to exhibit cytoplasmic sterility by E. D. P. Whelan and W. Dedio, Crop Science, Vol. 20, Nov.-Dec., 1980, p. 832, which is incorporated herein by reference.

By searching other varieties of *H. annuus*, a dominant gene for fertility restoration (Rf) was eventually found. It has since been discovered that most common wild sunflowers (also *H. annuus*) carry the restoring (Rf) gene. This gene (Rf) when introduced into the cytoplasmically sterile plant counteracts the cytoplasmic sterility, allowing the next generation of sunflowers to be fertile. This process is illustrated in FIG. 2. A plant having sterile cytoplasm 5 and which is not fertility restoring (rf rf) is crossed with a plant having any normal *H. annuus* or sterile *H. petiolaris* cytoplasm 7 and which is fertility restoring (RF RF). The result is a plant in which the cytoplasm 5 is sterile but the nucleus 1 contains the dominant fertility restoring gene (RF).

Dwarfism is one of a number of hybrid characteristics or traits considered desirable in sunflower. Dwarfism in sunflower is a condition wherein all plant parts are of normal size except that the internode length is reduced or shortened by about 35% to 50% of the standard length. Semi-dwarfism in a condition wherein the reduction in internode length is about 10% to 35% of the standard length. The height of the sunflower plant is often considered to be excessive and dwarf or semi-dwarf plants with shortened internode length are desired for several reasons. It is believed that in general shorter sunflower plants are less likely to bend or be damaged by wind or rain. It is also believed that if less plant energy is used to produce tall plants, more plant energy will be available for increased seed production.

Since until now dwarfism in sunflower has been controlled by recessive gene(s), it has been difficult to achieve satisfactory dwarf hybrids. A problem with working with a recessive gene (allele) in producing hybrid dwarf sunflowers is that unless both parent plants are homozygous for the recessive allele for dwarfism, the resulting seeds will produce standard size sunflowers. This can be further demonstrated using a Punnett Square which illustrates the possible genetic expressions for dwarfism in seed produced by various cross pollinations involving dwarfism. The horizontal line of the square shows the type of gene which can be donated to potential seeds by the male gametes. The genes donated by the female gametes are in the margin. The possible genotypes of the first generation of seeds ($F_1$) appear in the box and Table 1 illustrates the possible combinations that result when two plants both containing the dominant gene for standard internode length (Dw) are cross pollinated.

TABLE 1

|    | Dw    | Dw    |
|----|-------|-------|
| Dw | Dw Dw | Dw Dw |
| Dw | Dw Dw | Dw Dw |

The examples in Table 1 show that all seeds will carry the standard internode length and, therefore, will all produce plants having standard internode length.

Table 2 shows the results if one parent plant ($P_2$) contains one recessive allele for reduced internode length (Dw dw).

TABLE 2

|    | Dw    | dw    |
|----|-------|-------|
| Dw | Dw Dw | Dw dw |
| Dw | Dw Dw | Dw dw |

Although in this case 50% of the seeds have a recessive gene for dwarfism (Dw dw) none of them will produce shortened plants since each seed carries the Dw allele for standard internode length which dominates and controls the phenotype.

Table 3 illustrates the possible makeup of seeds from the cross pollination of two plants, one ($P_2$) containing both recessive alleles for reduced internode length (homozygous) (dw dw) and one ($P_1$) containing both dominant alleles for standard internode length (Dw Dw).

TABLE 3

|    | dw    | dw    |
|----|-------|-------|
| Dw | Dw dw | Dw dw |
| Dw | Dw dw | Dw dw |

In this case 100% of the seeds carry the recessive allele for reduced internode length but due to the pressence of the dominant gene (Dw) none would have the phenotype for reduced internode length.

Table 4 shows the case where each parent plant has one recessive gene (dw) for dwarfism. 25% of the seeds produced from the cross pollination will produce shortened plants with reduced internode length.

TABLE 4

|    | Dw    | dw    |
|----|-------|-------|
| Dw | Dw Dw | Dw dw |
| dw | Dw dw | dw dw |

Only in the case illustrated in Table 5 where both parents are homozygous for the recessive gene (dw) will all of the seeds produce shortened plants with reduced internode length.

TABLE 5

|    | dw    | dw    |
|----|-------|-------|
| dw | dw dw | dw dw |
| dw | dw dw | dw dw |

Several problems exist in producing dwarf hybrids in sunflowers especially using a recessive gene for dwarfism: (1) Since the gene for dwarfism (dw) is recessive, both parents must carry the gene in order to produce a hybrid with reduced internode length. This increases the research work and, therefore, reduces the number of potential hybrid combinations to be tested. (2) Since the same gene would be needed in both parents and would come from a single source, a number of other genes located nearby on the same chromosome (linkage)

would likely occur in both parental lines. This linkage effect would tend to reduce parental differences and result in decreased hybrid vigor. (3) Since inbred lines often produce smaller plants, dwarf inbreds which would have an additionally shortened stature could be less competitive with weeds, be more difficult to harvest, and have lower seed yields. (4) Fertilization could occur from any contaminating pollen of standard height sunflower (e.g., a farm field or a backyard garden). Pollen can be carried by insects up to several miles. Seed resulting from such contamination during the hybrid seed production would give rise to random tall plants in the subsequent commercial farm production. These tall plants are extremely visible and undesirable in a commercial sunflower field.

SUMMARY OF THE INVENTION

A novel semi-dwarf hybrid sunflower (*Helianthus annuus var. macrocarpus (DC.) Ckll.* (herein *H. annuus*)) seed and a method of producing the hybrid seed has now been found. The hybrid sunflower seed upon growth yields a semi-dwarf sunflower plant having a reduced internode length. The hybrid seed having been produced by cross pollinating a pair of parent plants $P_1$ and $P_2$ wherein in at least one parent substantially all pollen is nonfunctional and at least one parent has gametes with nuclei carrying at least one dominant gene for reduced internode length.

Sunflowers having gametes with nuclei which carry at least one dominant gene (Df) for semi-dwarfism or dwarfism have not previously been known. As discussed above prior to this invention dwarfism has previously been carried by a recessive gene (dw) and expressed only by a pair of the recessive genes (dw dw).

There are several advantages to using a dominant gene (Df) to produce semi-dwarf hybrids as compared to the known recessive gene (dw). (1) Only one parent need carry the gene semi-dwarfism in order to produce the semi-dwarf hybrid; (2) the problems from unwanted tall rogue hybrids produced by pollen from sources other than the desired male are avoided when the female (seed parent) line carries the dominant gene for semi-dwarfism; and (3) adverse chromosome linking relationships are avoided since the gene for semi-dwarfism does not come from both parents.

DETAILED DESCRIPTION OF THE INVENTION

Figure 1:
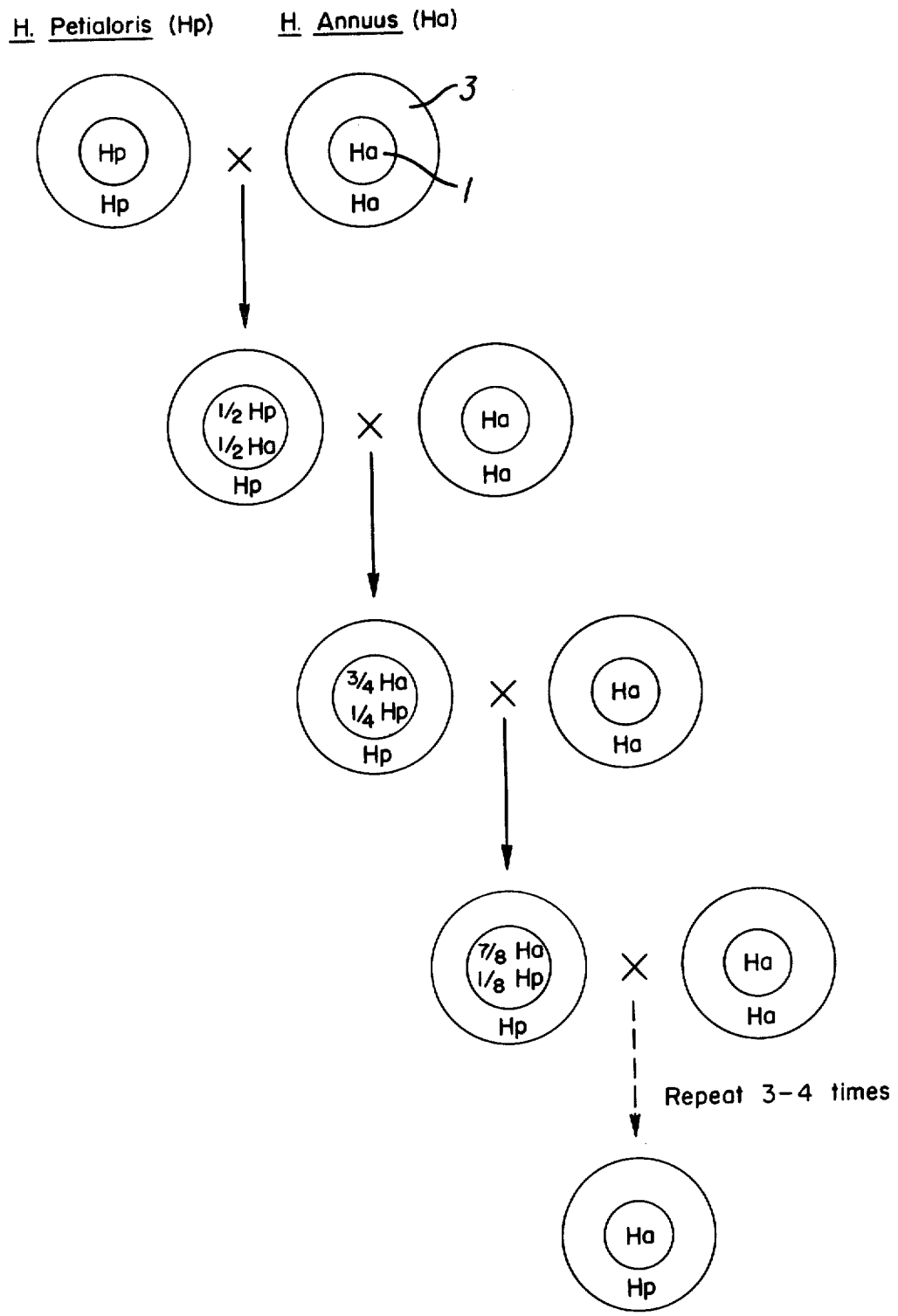
FIG. 1 is a cell diagram illustrating a known process of developing cytoplasmic sterility in sunflower.
Figure 2:
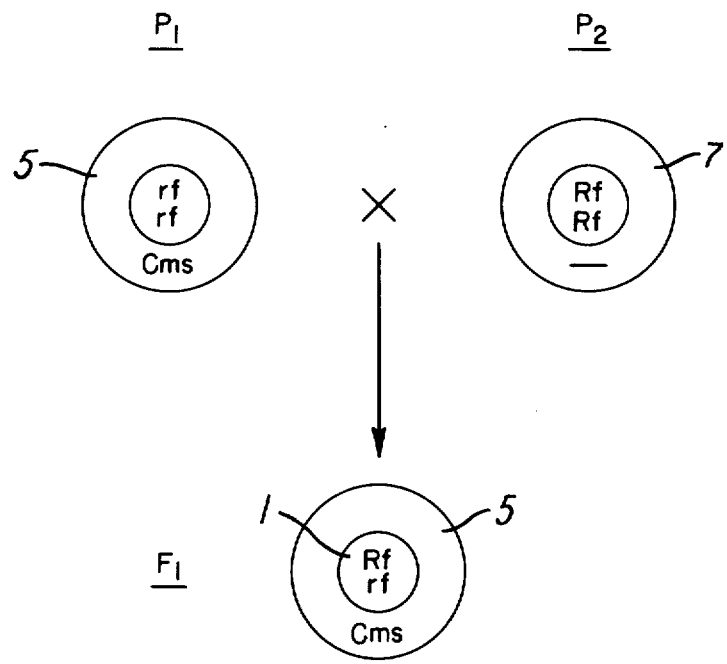
FIG. 2 is a cell diagram illustrating a known process of restoring fertility in sunflower.

Sunflower with the unique characteristics described above was discovered in the following manner:

Seeds from an Argentinian dwarf sunflower plant were grown and the resulting plants inbred to purify and strengthen the line. The Argentinian dwarf plant had been obtained as the result of a cross of a homozygous dwarf plant and a United States Department of Agriculture (herein USDA) restorer line known as RHA 273.

The Argentinian seeds were planted in Minnesota and self-pollinated under controlled conditions. The resulting plants had reduced internode length. Seeds were selected from the most attractive plants of this group and were planted in Chile and Texas during the next growing season. The resulting plants were incomplete dwarfs but had reduced internode length and a thickened stalk and were resistant to drought and stem disease. The seed from the most attractive plants were reserved and planted in California in the next season. The crop was selected for desirable plant type and allowed to self-pollinate. The seeds of this inbred line were harvested and designated as IR-10 (Imperial Restorer Line number 10) and were reserved for use in propagating the IR-10 plant stock. The plant (IR-10) produced by inbreeding of the original Argentinian dwarf sunflower has the following characteristics:

1. Height=85 cm (compared to 125 cm for standard USDA RHA 274).
2. Internode length=35 mm (compared to 48 mm for standard USDA RHA 274).
3. Multiflowered, carrying the recessive gene for branching (br br).
4. Has a stem diameter of 23 mm (compared to 17 mm for standard USDA RHA 274).
5. Flowers about 5 days later than standard USDA RHA 274 or 72 days following planting.
6. Has the normal dark yellow flower color.
7. Normal green stem color.
8. Black seeded.
9. Carries the fertility restoring gene (Rf Rf).
10. Carries one or more dominant genes (Df Df) for semi-dwarfism.
11. Carries the dominant gene for downy mildew resistance ($Pl_2$ $Pl_2$).
12. Carries genes for rust resistance.
13. Resistant to charcoal rot.

A sample of viable seed from inbred line IR-10 has been deposited at the United States Department of Agriculture National Seed Storage Laboratory, Fort Collins, Col., and has been assigned U.S. Ser. No. 117,846.

The California summer crop of IR-10 sunflowers described above in addition to being self-pollinated was also crossed to Cms HA89, a USDA released sunflower line which is a cytoplasmic sterile male. Cms HA89 has the following characteristics:

1. Height=118 cm (compared to 85 cm for IR-10 and to 125 cm for standard USDA RHA 274).
2. Internode length=42 mm (compared to 35 mm for IR-10 and 48 mm for standard USDA RHA 274).
3. Single flowered, carrying the Br Br gene for branching (non-branched version of the gene).
4. Has a stem diameter of 20 mm (compared to 23 mm for IR-10 and 17 mm for standard USDA RHA 274).
5. Flowers about 2 days later than the standard USDA RHA 274, but 3 days earlier than IR-10 or 69 days following planting.
6. Flowering time is sensitive to day length and flowering is delayed when the plant is grown during short day photoperiods.
7. Has the normal dark yellow flower color.
8. Normal green stem color.
9. Black seeded.
10. Carries sterile *H. petiolaris* cytoplasm.
11. Does not carry the fertility restoring gene Rf.
12. Carries a dominant gene or genes for resistance to verticillium wilt.
13. Is rust and downy mildew susceptible.
14. Has a high percentage of oil in the seed.
15. Has high general combining ability, i.e., gives excellent yields when crossed with a wide range of male lines.

16. Gives rise to normal height hybrids when crossed with standard USDA inbred male lines (e.g., RHA-274, RHA-271, RHA-273 and RHA-297).

This cross pollination experiment (Hybrid Cms HA89×IR-10) was conducted in order to examine the type of hybrids that IR-10 would produce. It was believed that the attractive plant type, resistance to drought and stem disease displayed in the earlier inbred plants would produce a commercially attractive hybrid for growth in dry areas. It was, of course, expected that when IR-10, which was assumed to carry a recessive gene for dwarfism, was crossed with Cms HA89, that the resulting hybrid would have standard internode length because the Cms HA89 parent has the dominant gene (Dw) for standard internode length.

The hybrid seeds from the above California cross pollination of IR-10 and Cms HA89 were collected and planted in Chile in the following winter. In February, the hybrid crop was observed in Chile. At maturity, under normal growing conditions, the hybrid plants (Cms HA89×IR-10), exhibited a reduced internode length of about 3" and resulting in about 18" shortening of plant height. The semi-dwarf hybrid which was produced from the hybrid seed, Cms HA89×IR-10 cross pollination, has been designated Imperial Experimental Hybrid 310. This semi-dwarf hybrid has the following characteristics:

1. Height=128 cm (compared to 157 cm for the standard USDA hybrid 894).
2. Internode length=75 mm (compared to 95 mm for the standard USDA hybrid 894).
3. Single flowered (BR br).
4. Has a stem diameter of 28 mm (compared to 23 mm for the standard USDA hybrid 894).
5. Flowers about one day later than the standard USDA hybrid 894, or 66 days after planting.
6. Has the normal dark yellow flower color.
7. Normal green stem color.
8. Black seeded.
9. Has normal fertile pollen (Rf rf).
10. Is semi-dwarf in plant height, the internode length being reduced about 22% in a subsequent South Texas Spring trial compared to the standard USDA hybrid 894.
11. Has approximately the same number of leaves as the standard USDA hybrid 894.
12. Has similar leaf size to the standard USDA hybrid 894.
13. Resistant to common North American downy mildew.
14. Carries dominant genes for rust resistance.
15. Carries dominant genes for verticillium wilt resistance.
16. Is resistant to charcoal rot.

Because this hybrid plant (Imperial Experimental Hybrid 310) exhibits a reduced internode length of about 10% to 35% when compared to standard sunflowers and Cms HA89 is known to carry the gene for standard plant size (Dw), it was determined that the nuclei of the somatic cells of IR-10 must carry homozygous genes for dwarfism which are dominant (Df Df) rather than recessive (dw dw) and that the nuclei of the gametes of IR-10 carry a dominant gene for dwarfism (Df). When crossed with Cms HA89 which carries the recessive allele for standard internode length (df) (herein sometimes referred to as nonsemi-dwarf), the resulting hybrid plant has the genotype (Df df) which was expressed as an attractive semi-dwarf hybrid:

TABLE 6

|    | Df    | Df    |
|----|-------|-------|
| df | Df df | Df df |
| df | Df df | Df df |

Table 6 is a schematic representation of the genetic cross if the dominant trait for reduced internode length is carried by only one gene. It is believed that the trait is carried by at least one dominant gene (Df) but it may be that semi-dwarfism in sunflowers is the expression of two or more genes (Table 7).

If two dominant genes are involved in producing the semi-dwarf hybrid, the Punnent square for the $F_1$ generation would be illustrated as follows:

TABLE 7

| ♀ | ♂ | |
|---|---|---|
|   | $df_1\ df_2$ | $df_1\ df_2$ |
| $Df_1\ Df_2$ | $Df_1\ df_1$ $Df_2\ df_2$ | $Df_1\ df_1$ $Df_2\ df_2$ |
| $Df_1\ df_2$ | $Df_1\ df_1$ $df_2\ df_2$ | $Df_1\ df_1$ $df_2\ df_2$ |
| all semi-dwarf and $Df_1\ df_1\ Df_2\ df_2$ | | |

The second generation $F_2$ or segregating generation resulting from self or sibling pollination (herein referred to as sib pollination) of the $F_1$ generation is illustrated by the following Punnet Square:

TABLE 8

|   | $Df_1\ Df_2$ | $Df_1\ df_2$ | $df_1\ Df_2$ | $df_1\ df_2$ |
|---|---|---|---|---|
| $Df_1\ Df_2$ | $Df_1\ Df_1$ $Df_2\ Df_2$ | $Df_1\ Df_1$ $Df_2\ df_2$ | $Df_1\ df_1$ $Df_2\ Df_2$ | $Df_1\ df_1$ $Df_2\ df_2$ |
| $Df_1\ df_2$ | $Df_1\ Df_1$ $df_2\ Df_2$ | $Df_1\ Df_1$ $df_2\ df_2$ | $Df_1\ df_1$ $df_2\ Df_2$ | $Df_1\ df_1$ $df_2\ df_2$ |
| $df_1\ Df_2$ | $df_1\ Df_1$ $Df_2\ Df_2$ | $df_1\ Df_1$ $Df_2\ df_2$ | $df_1\ df_1$ $Df_2\ Df_2$ | $df_1\ df_1$ $Df_2\ df_2$ |
| $df_1\ df_2$ | $df_1\ Df_1$ $df_2\ Df_2$ | $df_1\ Df_1$ $df_2\ df_2$ | $df_1\ df_1$ $df_2\ Df_2$ | $df_1\ df_1$ $df_2\ df_2$ |

Ratio 9 — $Df_1$— $Df_2$—
3 — $df_1\ df_1\ Df_2$—
3 — $Df_1$— $df_2\ df_2$
1 — $df_1\ df_1\ df_2\ df_2$ Table 8 illustrates several possibilities that exist in a two gene theory. If at least one of the two dominant genes involved is required to produce reduced internode length in sunflower, then the ratio of semi-dwarf to nonsemi-dwarf plants in $F_2$ would be 15 semi-dwarf plants to 1 nonsemi-dwarf plant. If both of the dominant genes involved are required for the reduced internode length in sunflower, then the ratio of semi-dwarf to nonsemi-dwarf plants in the $F_2$ generation would be 9 semi-dwarf plants to 7 nonsemi-dwarf plants.

If additive gene action is involved, that is where each dominant gene contributes only a portion of the internode length reduction, complete semi-dwarfism would occur only in the case where both the dominant genes, $Df_1$— $Df_2$—, are present. An intermediate type sunflower would be given by the presence of either one of the dominant genes, $Df_1$— $df_2\ df_2$ or $df_1\ df_1\ Df_2$—. Standard internode length would be expressed where the double recessive $df_1\ df_1\ df_2\ df_2$ is present. The results of additive gene action as described above and illustrated in the Punnet Square (Table 8) would give a ratio of 9 semi-dwarf plants to 6 intermediate shortened plants to 1 nonsemi-dwarf plant. Additional interpretations of this $F_2$ Punnet Square are possible.

Furthermore, it is possible that additional genes, modifying genes, chromosome linkages and environmental interactions may additionally complicate the explanation of the actual genetics of the dominant trait for reduced internode length. For example, it has been observed that high density plant populations may produce taller than expected sunflower plants.

In order to test the theory that the sunflower plant carrying the gene for semi-dwarfism does in fact produce a semi-dwarf hybrid with any standard height parent and is not only the expression of a single hybrid (Imperial Experimental Hybrid 310), a number of other hybrids using IR-10 have been made and are currently being fully evaluated. Some of the comparative data for these hybrid experiments are presented in Tables 9 to 12. These data were taken at onset of flowering prior to full internode extension.

TABLE 9

Hybrid Plant Height (cm)

| | ♂ | | | | |
|---|---|---|---|---|---|
| | Semi-Dwarf | Non-Semi-Dwarf | | | |
| ♀ | IR-10 | RHA-274 | RHA-273 | RHA-297 | AVERAGE |
| Cms HA89 | 128 | 157 | 150 | 166* | 150.25 |
| (Cms HA89 × HA300) | 124 | 154 | 153 | 148 | 144.75 |
| AVERAGE | 126 | 155.5 | 151.5 | 157 | 147.5 |
| CLASS AVERAGE | 126 | | 154.7 | | |
| ANOVA. | F. value | | C.V. = 5.10% | | |
| reps. | = 0.15 NS | | LSD. 5% = 12.1 | | |
| Hybrids | = 10.76** | | LSD. 1% = 16.3 | | |

*An estimated adjustment of a value from U.S. National Trial - Glyndon, Minn. 1981

TABLE 10

Hybrid Internode Length (mm)

| | ♂ | | | | |
|---|---|---|---|---|---|
| | Semi-Dwarf | Non-Semi-Dwarf | | | |
| ♀ | IR-10 | RHA-274 | RHA-273 | RHA-297 | AVERAGE |
| Cms HA89 | 75 | 95 | 110 | 104* | 96 |
| (Cms HA89 × HA300) | 75 | 86 | 101 | 86 | 87 |
| AVERAGE | 75 | 90.5 | 105.5 | 95 | 91.5 |
| CLASS AVERAGE | 75 | | 97 | | |
| ANOVA. | F. value | | C.V. = 8.35% | | |
| reps. | = 0.66 NS | | LSD. 5% = 13.2 | | |
| Hybrids | = 9.90** | | LSD. 1% = 18.3 | | |

*An estimated adjustment of a value from U.S. National Trial - Glyndon, Minn. 1981

Tables 9 and 10 compare two hybrids made using IR-10 with 6 hybrids prepared using the same two female parents, and three standard inbred male lines. Table 9 gives the resulting plant height (cm) and Table 10 gives the internode lengths (mm) of the hybrids. The hybrid heights and internode lengths from the IR-10 crosses were significantly different from those of the standard hybrids. The data in Tables 9 and 10 were taken from a larger study and represent only the hybrids where direct parental comparisons can be made. The accompanying statistics, however, apply to the total study.

The results set forth in Tables 9 and 10 indicate that: (1) varying the female parent generally had little effect on plant height and internode length; (2) varying the standard male parent (RHA 274, 273, 297) had minimal effect on plant height or internode length; (3) the male line IR-10 gave reduced plant height and internode length for the two seed parent lines and differed significantly from the plant height and internode length for the other three male lines.

Additional data from the comparative hybrid study discussed above are set forth in Tables 11 and 12. These hybrid could not be compared directly with each other as in Tables 9 and 10 because of varying parental combinations.

The same statistics given from Table 9 apply equally to Tables 11 and 12.

TABLE 11

| NonSemi-Dwarfs | |
|---|---|
| Hybrid | Plant Height (cm) |
| USDA - 894 (Cms HA89 × R-274) | 157 |
| USDA - 893 (Cm HA89 × R-273) | 150 |
| (Cms HA89 × HA300) × RHA-273 | 153 |
| (Cms HA89 × HA300) × RHA-274 | 154 |
| (Cms HA98 × HA300) × RHA-297 | 148 |
| Sigco - 449 | 169 |
| Cargill - 206 | 152 |
| AVERAGE | 155 |

TABLE 12

| Semi-Dwarf Hybrids | |
|---|---|
| Hybrid | Plant Height (cm) |
| Cms HA89 × IR-10 | 128 |
| Cms HA99 × IR-10 | 124 |
| Cms HA300 × IR-10 | 142 |
| Cms HA224 × IR-10 | 136 |
| (Cms HA89 × HA300) × IR-10 | 124 |
| (Cms HA89 × HA124) × IR-10 | 131 |
| (Cms HA89 × HA303) × IR-10 | 136 |
| AVERAGE | 132 |

The data in Tables 11 and 12 indicate that the gene for semi-dwarfism found in IR-10 will give semi-dwarf hybrids when crossed with different sterile inbred lines or sterile hybrids. As a group the resulting semi-dwarf hybrids have significantly shorter stature than do somewhat similar commercial hybrids grown in the same environment.

In these examples IR-10 which carries the dominant gene for semi-dwarfism (Df), and the restoring fertility gene (Rf Rf) gives attractive semi-dwarf hybrid plants with reduced height and thick stems. This invention is not, however, limited to the use of the dominant gene (Df) in the IR-10 male line. The dominant gene (Df) can be transferred to other existing male inbred lines by standard plant breeding techniques, for example back crossing. New male fertility restoring inbred lines utilizing the dominant gene could also be developed by standard plant breeding techniques, for example crossing and subsequent inbreeding.

It is also possible to transfer the dominant gene or genes for semi-dwarfism into inbred lines not carrying the fertility restoring gene. Such lines can be developed in normal (H. annuus) cytoplasm as well as their sterile counterparts in H. petiolaris cytoplasm. These inbred lines could then be used to develop semi-dwarf hybrids, regardless of the presence or absence of semi-dwarfism in a fertility restoring line.

Furthermore, such semi-dwarf nonrestoring lines could be used to produce semi-dwarf synthetic varieties, or specific semi-dwarf open pollinated varieties. A synthetic variety could be developed by interpollinating at least two inbred or hybrid lines, and preferably four to twelve lines, having gametes with nuclei carrying at least one dominant gene for reduced internode length for two or more generations, and preferably four to six generations. In order to produce a variety it is necessary to continually interpollinate the inbred or hybrid plants being used for several generations. The plants resulting from this technique, unlike the semi-dwarf hybrids described previously, not only carry the dominant gene for semi-dwarfism but can be maintained by open pollination to produce subsequent generations.

I claim:

1. A method of producing semi-dwarf hybrid sunflower seeds which will produce sunflowers with reduced internode length under normal growing conditions, which comprises:
   (a) growing a pair of parent plants ($P_1$ and $P_2$) wherein in at least one parent substantially all pollen is nonfunctional and at least one parent has gametes with nuclei which carry at least one dominant gene for reduced internode length (Df);
   (b) cross pollinating the plants ($P_1 + P_2$) to produce hybrid seeds $F_1$; and
   (c) harvesting the hybrid seeds.

2. A method as described in claim 1 wherein substantially all pollen in the female seed plant ($P_1$) is made nonfunctional by the use of plant breeding techniques selected from the group consisting of chemical gametocides, genetic sterility, partial pollen abortion and self-incompatibility.

3. A method of producing semi-dwarf hybrid sunflower seeds which will produce sunflowers with reduced internode length under normal growing conditions, which comprises:
   (a) growing a female seed parent plant ($P_1$) in which substantially all pollen is nonfunctional, having gametes with nuclei which carry a gene for standard internode length (df);
   (b) growing a male pollen bearing parent plant ($P_2$) having gametes with nuclei which carry at least one dominant gene for reduced internode length (Df);
   cross pollinating the plants ($P_1$ and $P_2$) to produce hybrid seeds $F_1$; and
   (d) harvesting the hybrid seeds.

4. A method as described in claim 3 wherein $P_1$ is a cytoplasmic sterile plant which is not fertility restoring having gametes with nuclei which carry a gene for standard internode length (df) and $P_2$ has gametes with nuclei carrying a fertility restoring gene (Rf) and at least one dominant gene for reduced internode length (Df).

5. A method of producing semi-dwarf hybrid sunflower seeds which will produce sunflower with reduced internode length under normal growing conditions, which comprises:
   (a) growing a female seed parent plant ($P_1$) in which substantially all pollen is nonfunctional, having gametes with nuclei which carry as least one dominant gene for reduced internode length (Df);
   (b) growing a male pollen bearing parent plant ($P_2$) having gametes with nuclei which carry a gene for standard internode length (df);
   (c) cross pollinating the plants ($P_1$ and $P_2$) to produce hybrid seeds $F_1$; and
   (d) harvesting the hybrid seeds.

6. A method as described in claim 5 wherein $P_1$ is a cytoplasmic sterile plant which is not fertility restoring having gametes with nuclei which carry at least one dominant gene for reduced internode length (Df) and $P_2$ has gametes with nuclei carrying a fertility restoring gene (Rf) and a gene for standard internode length (df).

7. A method of producing semi-dwarf hybrid sunflower seeds which will produce sunflower with reduced internode length under normal growing conditions, which comprises:
   (a) growing a female seed parent plant ($P_1$) in which substantially all pollen is nonfunctional, having gametes with nuclei which carry at least one dominant gene for reduced internode length (Df);
   (b) growing a male pollen bearing parent plant ($P_2$) having gametes with nuclei which carry at least one dominant gene for reduced internode length (Df);
   (c) cross pollinating the plants ($P_1$ and $P_2$) to produce hybrid seeds $F_1$; and
   (d) harvesting the hybrid seeds.

8. A method as described in claim 7 wherein $P_1$ is a cytoplasmic sterile plant which is not fertility restoring having gametes with nuclei which carry at least one dominant gene for reduced internode length (Df) and $P_2$ has gametes with nuclei carrying a fertility restoring gene (Rf) and at least one dominant gene for reduced internode length (Df).

9. A method of producing semi-dwarf inbred sunflower seeds which will produce sunflowers with reduced internode length under normal growth conditions, which comprises:
   (a) growing a plant having gametes with nuclei which carry at least one dominant gene for reduced internode length (Df);
   (b) sib pollinating the plant; and
   (c) harvesting the hybrid seed.

10. A semi-dwarf hybrid sunflower seed which upon growth yields a sunflower plant having a reduced internode length, the hybrid seed having been produced by cross pollinating a pair of parent plants ($P_1$ and $P_2$), wherein in at least one parent substantially all pollen is nonfunctional and at least one parent has gametes with nuclei which carry at least one dominant gene for reduced internode length (Df).

11. A semi-dwarf hybrid sunflower seed as described in claim 10 wherein substantially all pollen in the female seed plant ($P_1$) is made nonfunctional by the use of plant breeding techniques selected from the group consisting of chemical gametocides, genetic sterility, partial pollen abortion and self-incompatibility.

12. A semi-dwarf sunflower seed as described in claim 10 wherein the internode length is reduced by about 10% to 35% as compared to hybrids having standard internode length.

13. A semi-dwarf hybrid sunflower seed as described in claim 10 wherein the internode length of the plant is about 75 mm.

14. A semi-dwarf hybrid sunflower seed which upon growth yields a sunflower plant having a reduced internode length, the hybrid seed having been produced by cross pollinating two sunflower plants, wherein the female seed parent plant ($P_1$) produces pollen which is substantially all nonfunctional, and $P_1$ has gametes with nuclei which carry a gene for standard internode length (df); and the other parent plant $P_2$ having gametes with nuclei carrying at least one dominant gene for reduced internode length.

15. A semi-dwarf hybrid sunflower seed as described in claim 11 wherein $P_1$ is a cytoplasmic sterile plant which is not fertility restoring having gametes with nuclei which carry a gene for standard internode length (df) and $P_2$ has gametes with nuclei carrying a fertility restoring gene (Rf) and at least one dominant gene for reduced internode length (Df).

16. A semi-dwarf hybrid sunflower seed which upon growth yields a sunflower plant having a reduced internode length, the hybrid seed having been produced by cross pollinating two sunflower plants, wherein the female seed parent plant ($P_1$) produces pollen which is substantially all nonfunctional, and $P_1$ has gametes with nuclei which carry a dominant gene for reduced internode length (Df); and the other parent plant $P_2$ having has gametes with nuclei carrying a gene for standard internode length.

17. A semi-dwarf hybrid sunflower seed as described in claim 12 wherein $P_1$ is a cytoplasmic sterile plant which is not fertility restoring having gametes with nuclei which carry at least one dominant gene for reduced internode length (Df) and $P_2$ has gametes with nuclei carrying a fertility restoring gene (Rf) and a gene for standard internode length (df).

18. A semi-dwarf hybrid sunflower seed which upon growth yields a sunflower plant having a reduced internode length, the hybrid seed having been produced by cross pollinating two sunflower plants, wherein the female seed parent plant ($P_1$) produces pollen which is substantially all nonfunctional, and $P_1$ has gametes with nuclei which carry at least one dominant gene for reduced internode length (Df); and the other parent plant $P_2$ having has gametes with nuclei carrying at least one dominant gene for reduced internode length (Df).

19. A semi-dwarf hybrid sunflower seed as described in claim 18 wherein $P_1$ is a cytoplasmic sterile plant which is not fertility restoring having gametes with nuclei which carry at least one dominant gene for reduced internode length (Df) and $P_2$ has gametes with nuclei carrying a fertility restoring gene (Rf) and at least one dominant gene for reduced internode length (Df).

20. A first generation semi-dwarf hybrid sunflower plant of reduced internode length, the hybrid sunflower plant having been grown from the seed from the cross pollination of a pair of parent plants ($P_1$ and $P_2$) wherein in at least one parent substantially all pollen is nonfunctional and at least one parent has gametes with nuclei which carry at least one dominant gene for reduced internode length (Df).

21. A semi-dwarf sunflower plant as described in claim 20 wherein the internode length is reduced by about 10% to 35% as compared to hybrids having standard internode length.

22. A semi-dwarf hybrid sunflower plant as described in claim 20 wherein the internode length is about 75 mm.

23. A method of producing seeds of a semi-dwarf sunflower variety which will produce sunflower with reduced internode length in successive generations under normal growing conditions, which comprises:

(a) growing at least two inbred lines each having gametes with nuclei carrying at least one dominant gene for reduced internode length;

(b) interpollinating the inbred lines from step (a) for at least two generations; and (c) harvesting the seeds.

24. A method of producing seeds of a semi-dwarf sunflower variety which will produce sunflower with reduced internode length in successive generations under normal growing conditions, which comprises:

(a) growing at least two hybrid lines each having gametes with nuclei carrying at least one dominant gene for reduced internode length;

(b) interpollinating the hybrid lines from step (a) for at least two generations; and (c) harvesting the seeds.

* * * * *